United States Patent
Rodríguez et al.

(10) Patent No.: US 11,179,455 B2
(45) Date of Patent: Nov. 23, 2021

(54) USE OF A GROWTH HORMONE SECRETAGOGUE PEPTIDE AS A VACCINE ADJUVANT

(71) Applicant: CENTRO DE INGENIERIA GENÉTICA BIOTECNOLOGIA, Havana (CU)

(72) Inventors: Rebeca Martínez Rodríguez, Havana (CU); Liz Hernandez Perez, Havana (CU); Lázaro Gil González, Mayabeque (CU); Yamila Carpio González, Havana (CU); Mario Pablo Estrada García, Havana (CU)

(73) Assignee: CENTRO DE INGENIERIA GENÉTICA BIOTECNOLOGIA, Havana (CU)

( * ) Notice: Subject to any disclaimer, the term of this patent is extended or adjusted under 35 U.S.C. 154(b) by 0 days.

(21) Appl. No.: 16/346,034

(22) PCT Filed: Oct. 30, 2017

(86) PCT No.: PCT/CU2017/050006
§ 371 (c)(1),
(2) Date: Apr. 29, 2019

(87) PCT Pub. No.: WO2018/082719
PCT Pub. Date: May 11, 2018

(65) Prior Publication Data
US 2020/0353065 A1 Nov. 12, 2020

(30) Foreign Application Priority Data
Nov. 1, 2016 (CU) .............................. CU2016-0161

(51) Int. Cl.
| A61K 39/12 | (2006.01) |
| A61P 31/12 | (2006.01) |
| A61K 38/25 | (2006.01) |
| A61K 39/00 | (2006.01) |

(52) U.S. Cl.
CPC .............. *A61K 39/12* (2013.01); *A61K 38/25* (2013.01); *A61K 39/0003* (2013.01); *A61P 31/12* (2018.01); *A61K 2039/552* (2013.01); *A61K 2039/70* (2013.01)

(58) Field of Classification Search
None
See application file for complete search history.

(56) References Cited

PUBLICATIONS

Martinez et al. A novel GH secretagogue, A233, exhibits enhanced growth activity and innate immune system stimulation in teleosts fish. Journal of Endocrinology (2012) 214, 409-419.*
Uribe et al. Innate and adaptive immunity in teleost fish: a review. Veterinarni Medicina, 56, 2011 (10): 486-503.*
Thim et al. Vaccine Adjuvants in Fish Vaccines Make a Difference: Comparing Three Adjuvants (Montanide ISA763A Oil, CpG/Poly l:C Combo and VHSV Glycoprotein) Alone or in Combination Formulated with an Inactivated Whole Salmonid Alphavirus Antigen. Vaccines 2014, 2, 228-251.*
Martinez et al. Oral administration of the growth hormone secretagogue-6 (GHRP-6) enhances growth and non-specific immune responses in tilapia (*Oreochromis* sp.). Aquaculture 452 (2016) 304-310.*

* cited by examiner

*Primary Examiner* — Nianxiang Zou
(74) *Attorney, Agent, or Firm* — Hoffmann & Baron, LLP (57) ABSTRACT

The present invention is related to the use of the GHRP-6 and one structural analogue as molecular adjuvants for vaccines. Among other applications, these vaccines may be employed for preventing diseases caused by infectious agents, like viruses, bacteria and ectoparasites, that affect mammals, birds and aquatic organisms. The GHRP-6 and its analogue A233 are effectives as adjuvants when they are combine with a given antigen, since they enhance the specific immune response against it.

8 Claims, 4 Drawing Sheets
Specification includes a Sequence Listing.

USE OF A GROWTH HORMONE SECRETAGOGUE PEPTIDE AS A VACCINE ADJUVANT

CROSS-REFERENCE TO RELATED APPLICATIONS

This application is a National Stage Application that claims a benefit of priority from Application No. PCT/CU2017/050006 filed Oct. 30, 2017, which claims priority to Application No. CU 2016-0161, filed Nov. 1, 2016, the disclosures of which are herein incorporated in their entirety.

TECHNICAL FIELD

The present invention is related to the field of molecular biology and immunology, specifically, with the development of vaccines and adjuvants for them. In particular, the present invention discloses the use of a growth hormone secretagogue peptide, selected from the synthetic growth hormone releasing peptide GHRP-6 and its structural analogue A233, as a molecular adjuvant for vaccines.

BACKGROUND OF THE INVENTION

Growth hormone secretagogues (GHSs) (Davenport et al. 2005, *Pharmacol. Rev.* 57: 541-546) are a family of compounds that includes peptidyl and non-peptidyl molecules that stimulate the secretion of growth hormone (GH) in vitro and in vivo (Tannenbaum and Bowers, 2001, *Endocrine* 14: 21-27). Ghrelin is the endogenous ligand for the growth hormone secretagogues receptor (GHS-R) (Kojima et al., 1999, *Nature* 402: 656-660). It is involved in multiple processes, including regulation of energy balance, appetite, metabolic signals, among others (Dixit and Taub, 2005, *Exp. Gerontoly* 40: 900-910). In addition, it exerts anti-inflammatory actions, modulates phagocytosis and promotes thymopoiesis, as well as the attenuation of septic shock (Hattori, 2009, *J. Clin. Endocrinol. Metab.* 86: 4284-4291).

GHS, in addition to stimulating the GH secretion, regulate the appetite and weight gain in mammals, birds and fish (Kaiya et al., 2008, *Comp. Biochem. Physiol.* A 149: 109-128). They also have cardioprotective properties, by improving cardiac function variables in several studies in vivo, and inhibiting the proliferation of cancer cells (Locatelli and Rossoni, 1999, *Endocrinol.* 140:4024-4031; Tivesten and Bollano, 2000, *Endocrinol.* 141: 60-66; Cassoni et al., 2001, *J. Clin. Endocrinol. Metab.* 86: 1738-1745). Furthermore, they are involved in processes such as inflammation and aging (Hattori, 2009, *J. Clin. Endocrinol. Metab.* 86: 4284-4291).

It is known that the hexamer GHRP-6 (whose amino acid sequence is His-D-Trp-Ala-Trp-D-Phe-Lys-NH2) is extremely potent, and safe, by triggering the release of growth hormone in mammals and birds (Bowers et al., 1984, *Endocrinol.* 114: 1537-45), as well as in crustaceans (European Patent No. EP1477181 B1).

In animal models, examples of anti-inflammatory effects of ghrelin have been described (Smith et al., 2005, *Trends Endocrinol. Metab.* 16, 436-442). In most of those studies, it has been suggested that the use of acylated ghrelin suppressed the expression and/or production of pro-inflammatory cytokines, in spite of the pathology or the dose, and of the treatment schedule used (Baatar et al., 2011, *Molecular and Cellular Endocrinology* 340: 44-58). Its role in the attenuation of mortality and of the inflammatory effects caused by lipopolysaccharides (LPS), both in vivo and in vitro, as well as of sepsis in rodent models has been previously proposed (Dixit et al., 2004, *J. Clin. Invest.* 114: 57-66; Taub, 2007, *Vitam. Horm.* 77: 325-346).

In studies conducted in murine models of chronic inflammation, ghrelin and the synthetic agonist GHRP-2 significantly inhibited the release of interleukin 6 (IL-6) and nitric acid from activated macrophages, and attenuated the arthritis (Granado et al., 2005, *Am. J. Physiol. Endocrinol. Metab.* 288: E486-E492). Also, similar studies that have been performed have evidenced their anti-inflammatory effects (González-Rey et al., 2006, *Gastroenterol.* 130 (6), 1707-1720).

In a work performed by Lofti and co-workers in 2011 (Lofti et al., 2011, *Kafkas Univ Vet Fak Derg* 17 (6): 949-952), the injection of ghrelin in ovo had influence in the leukocyte differential counting in newly hatching chickens. With a dose of 100 ng, on day 10 of incubation, it caused an increase in the count of heterophil, basophils and eosinophils, and in the heterophil/lymphocyte ratio, while it decreased the lymphocytes.

In the case of teleosts, in vitro studies have shown that the treatment of rainbow trout leucocytes (*Oncorhynchus mykiss*) with ghrelin increases the production of superoxide anion, the levels of GH messenger ribonucleic acid, and superoxide dismutase in these cells (Yada et al., 2006, *Endocrinol.* 189: 57-65). In that study, it was reported that prior incubation with the [D-Lys3]-GHRP-6 secretagogue receptor antagonist, and the immune-neutralization of GH, decreased the production of this reactive oxygen species ($O^{2'}$—), which suggests that the effects of ghrelin on leukocytes are mediated by GH secretion (Yada et al., 2007, *Endocrinol.* 152: 353-358). On the other hand, in vitro studies carried out with a GHRP-6 analogue secretagogue peptide, A233, showed that the production of indicators of phagocytic activity, such as superoxide anion, in tilapia leukocytes (*Oreochromis* sp.) (Martínez et al., 2012, *J. of Endocrinol.* 214: 409-419) was stimulated. In the same study, it was evidenced that the administration of A233, by immersion baths, stimulates parameters of the antioxidant defense with the enzyme superoxide dismutase in tilapia larvae (*Oreochromis* sp.), as well as the lectin titers and the antiprotease activity. In other experiments, performed in juvenile tilapia, orally fed with GHRP-6, there was an increase in lectin titers, and in the number of intraepithelial lymphocytes of the gastric mucosa (Martínez et al., 2016, *Aquaculture* 452 304-310). This latter parameter is related to the innate immune system, is non-specific, and is not related to the administration of a particular antigen.

Protective immunity against different pathogens requieres responses that can be generated with the appropriate vaccine adjuvant (Awate et al., 2013, *Frontiers in Immunology* 4: 1-10). It is therefore necessary to identify and develop novel adjuvants, to address the development of vaccines against pathogens that have so far been refractory to traditional vaccination strategies and to overcome the limitations of the few available licensed adjuvants (Harandi et al., 2010, *Vaccine* 28(12):2363-6; Pérez et al., 2012, *Braz J Med Biol Res* 45(8):681-92).

Many adjuvants potentiate a strong unspecific inflammatory response, increase the immunogenicity of co-administered antigens, but may also cause unwanted effects, then it is necessary to develop new adjuvants that elicit a more specific and direct immune response, to obtain an optimal and safe protection conferred by the vaccines.

DETAILED DESCRIPTION OF THE INVENTION

The present invention solves the above mentioned problem, by providing an adjuvant able to effectively enhance the immune response to a co-administered antigen. The invention discloses the use of a growth hormone secretagogue peptide, identified as SEQ ID No. 1 (GHRP-6) or SEQ ID No. 2 (A233), as a molecular adjuvant in the manufacture of a vaccine that is used in different immunization strategies. In one embodiment of the invention said vaccine is used in the prevention of diseases caused by infectious agents. In a particular embodiment, these diseases affect mammals, birds or fish; and the infectious agents can be viruses, bacteria and ectoparasites, among others.

In the context of this invention, the term "molecular adjuvant" refers to a substance capable of positively modulating the immune response against a vaccine antigen, resulting in an increase thereof. Up-to-date there is no research demonstrating or suggesting the use of ghrelin, nor analogues thereof, as a molecular adjuvant. In contrast, the use of ghrelin for the treatment of inflammatory diseases has been proposed (González-Rey et al., 2006, *Gastroenterology* 130 (6), 1707-1720; Baatar et al., 2011, *Mol Cell Endocrinol* 340: 44-58). Having into account this existing knowledge, it is unexpected the effect found in the present invention, that demonstrates that the administration of GHRP-6 or A233, in combination with a vaccine antigen, stimulates the specific immune response against said antigen.

In another embodiment, a vaccine composition comprising a growth hormone secretagogue peptide identified as SEQ ID No.1 (GHRP-6) or SEQ ID No.2 (A233), at least a vaccine antigen, and pharmacologically accepted vehicles or diluents is also described. The vaccine composition of the invention may comprise other compounds which act as vaccine adjuvants that are known to those skilled in this technical field. Within these adjuvants are, for example, aluminum salts and oily adjuvants.

In order to illustrate different embodiments of the invention, the vaccine compositions therein included various antigens and the GHRP-6 or A233 peptides. Among the antigens that are combined with GHRP-6 or its structural analogue A233 are ovalbumin (OVA), the Dengue 2 virus capsid protein (C2), the pP0 peptide from *Rhipicephalus sanguineus* (Rodríguez-Mallón et al., 2012; *Vaccine* 30: 1782-1789), the chimeric protein P0-my32 (fusion polypeptide of two antigens of *Lepeophtheirus salmonis*), and the fusion polypeptide of P0 from *L. salmonis* and T-cell epitopes (P0-TT). Without being a limitation to the invention, the compositions were administered to mice, birds and fish, and for the first time an adjuvant effect was demonstrated for said secretagogues. Unexpectedly, it was observed that administration of GHRP-6 or A233 combined with an antigen increases antigen-specific antibody levels, in several animals species.

In one embodiment of the invention, the vaccine antigen is selected from the group consisting of peptides, proteins, virus and attenuated bacteria. In one preferred embodiment of the invention, said vaccines are administered to mammals, birds or fish. In a more preferred embodiment, the vaccine composition of the invention is administrable orally or by injection. In a particular embodiment, in the vaccine composition, the peptide of SEQ ID No.1 or SEQ ID No.2 is in a concentration of 50-600 µg/Kg of formulated feed, when the vaccine is orally administered to fish.

The invention also discloses a method for increasing the immune response against a vaccine antigen, which is characterized by the administration of an effective amount of a growth hormone secretagogue peptide, identified as SEQ ID No. 1 (GHRP-6) or SEQ ID No.2 (A233), as a molecular adjuvant of said antigens. In one embodiment of the invention, the vaccine antigen is used for the prevention of diseases caused by infectious agents. In a particular embodiment of said method, the peptide of sequence SEQ ID No. 1 or SEQ ID No. 2 is employed at 50-600 µg/Kg of formulated feed, when the vaccine antigen and the adjuvant peptide are administered orally. In another embodiment of said method, the peptide of sequence SEQ ID NO. 1 or SEQ ID No. 2 is employed at 0.1-40 µg/g of the animal body weight, if the vaccine antigen and the peptide acting as a molecular adjuvant are administered by injection. For the purpose of the invention, the peptides GHRP-6 and A233, known GH secretagogues, are obtained by chemical synthesis.

As shown in various embodiments of the invention, the increase in the immune response against the antigen of interest brings higher levels of protection against various infectious agents, including viral, bacterial and ectoparasite entities.

EXAMPLES

Example 1

Effect of Co-Administration of GHRP-6 on the Humoral Immune Response Against OVA Thirty-six female BALB/c mice were used. Six study groups, with 6 animals each, were separated. Three groups were immunized by s.c route and the rest of them were treated by i.p route. In all groups, the immunogens were emulsified with Freund's adjuvant.

Group 1: Placebo (phosphate buffered saline, abbreviated PBS). s.c route.
Group 2: Placebo (PBS). i.p. route.
Group 3: GHRP-6 at 10 µg/animal and OVA at 5 µg/animal. s.c. route.
Group 4 GHRP-6 at 10 µg/animal and OVA at 5 µg/animal. i.p route.
Group 5: OVA 5 µg/animal. s.c. route.
Group 6: OVA 5 µg/animal. i.p. route.

Figure 1:
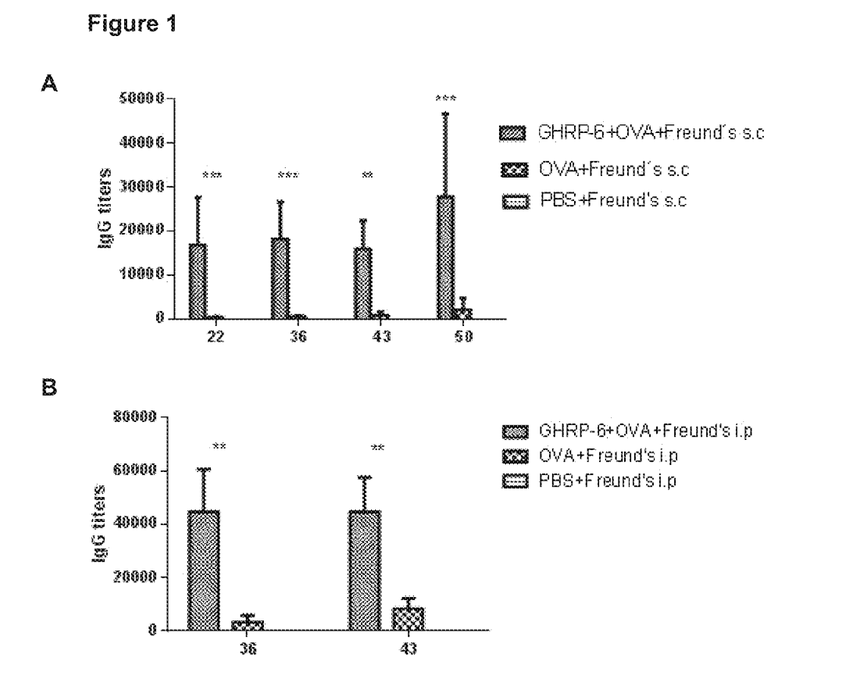
FIG. 1. Antibody response in mice immunized with OVA, GHRP-6 and Freund's adjuvant, or with OVA and Freund's adjuvant. A. Titers of immunoglobulin G (IgG) in groups immunized by subcutaneous route (s.c). B. Titers of IgG in groups immunized by intraperitoneal route (i.p). The median and the standard deviation within each group are represented.  indicates $p<0.0014$; * indicates $p<0.001$.

Mice received 150 µL of the immunogen in all groups, which was administered to the animals on days 1 and 15 of the immunization schedule. Blood extractions were performed on days 0 (pre-immune serum), 8, 15, 22, 36, 43 and 50. Total IgG titers, IgG1 and IgG2a were evaluated. Complete Freund's Adjuvant (CFA) was used in the first immunization and Incomplete Freund's Adjuvant (IFA) in the next one. The animals of the group immunized with GHRP-6 and OVA, by s.c route, had higher titers (with statistical significance: p<0.05) than those of the group receiving OVA without GHRP-6, by the same route, on days 22, 36, 43 and 50 of the experiment (FIG. 1A). Animals injected with the same immunogens, but by i.p. route, had the same behavior on days 36 and 43 of the experiment (FIG. 1 B).

Figure 2:
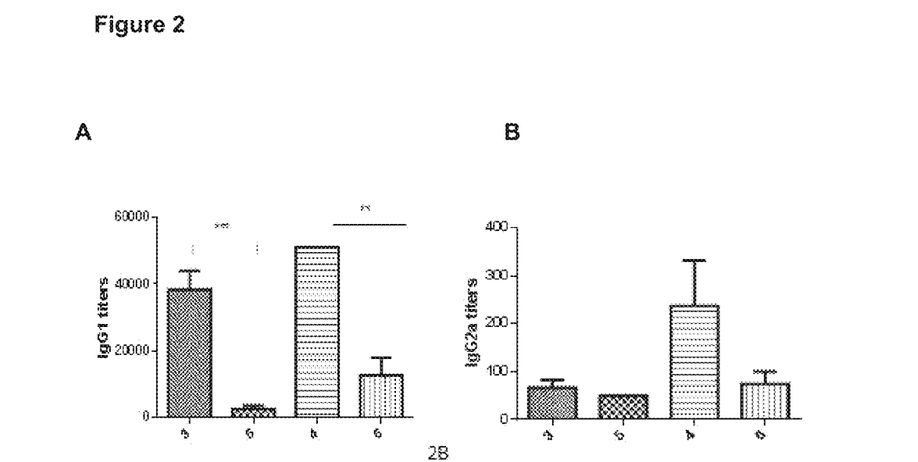
FIG. 2. Antibody response in mice immunized with OVA, GHRP-6 and Freund's adjuvant, by s.c and i.p routes. (Groups 3 and 4, respectively); or with OVA and Freund's adjuvant, by s.c and i.p routes (Groups 5 and 6 respectively). A. Titers of IgG1. B. Titers of IgG2a. The median and the standard deviation within each group are represented.  indicates $p<0.0014$; * indicates $p<0.001$.

IgG1 and IgG2a titers were determined in the serum extracted on day 36, in groups immunized with OVA with or without GHRP-6, by s.c and i.p routes. (FIGS. 2A and 2B). No significant differences were observed in IgG2a titers between the groups treated with GHRP-6 and those that did not receive said secretagogue, for both routes of administration (FIGS. 2A and 2B). Significant differences were observed for IgG1 in both administration routes, being higher in the groups vaccinated in the presence of GHRP-6.

The ratio IgG1/IgG2a, as a measure of the differencial reactivity towards a Th2 or Th1 response, respectively, was significantly superior in the group immunized by i.p route, with OVA in the presence of GHRP-6 and Freund's adjuvant, compared to the group injected with OVA and Freund's adjuvant only. This ratio is shown in Table 1, where data represent the mean of the IgG1/IgG2a ratio corresponding to the six animals in the group.

TABLE 1

Ratio IgG1/IgG2a in both groups immunized by intraperitoneal route.

| Immunogen of the group | IgG1/IgG2a |
| --- | --- |
| GHRP-6 + OVA + Freund's adjuvant | 981.33* |
| OVA + Freund's adjuvant | 172.33 |

*indicates significant differences p < 0.05.

Example 2

Effect of the Co-Administration of the Peptide A233 on the Humoral Immune Response Against OVA To evaluate whether the peptide A233 exerts an adjuvant effect on OVA, 18 female BALB/c mice were used. Mice received 150 µL of immunogen in all groups, by i.p route, which was given to the animals on days 1 and 15 of the immunization schedule. Blood samples were taken at days 0 (preimmune serum), 8, 15, 22, 36, 43 and 50. The titers of total IgG present in the sera were evaluated. The animals were immunized with 5 µg OVA/animal and 10 µg A233/animal (Group 2), or with 5 µg of OVA/animal (Group 3). The control group was injected with PBS (Group 1). All immunogens were emulsified with Freund's adjuvant.

Figure 3:
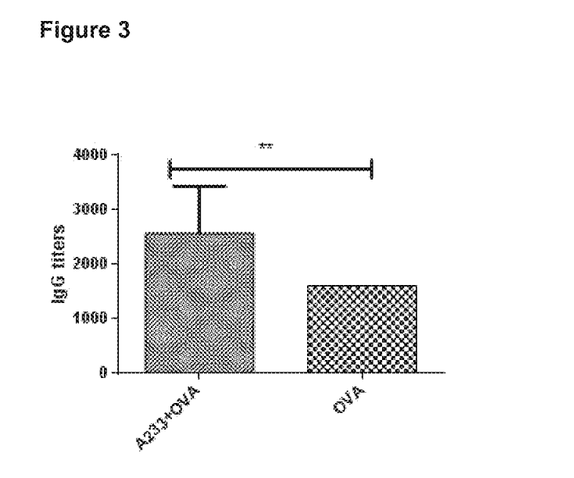
FIG. 3. IgG titers in mice immunized with A233 peptide, OVA and Freund's adjuvant; or OVA and Freund's adjuvant, by i.p route. The levels of antibodies detected in serum extracted on day 22 of the immunization schedule are shown. The median and the standard deviation within each group are represented. ** indicates $p<0.0014$.

In animals injected with OVA and the peptide A233 there was a significant increase in anti-OVA antibody titers, in comparison with those immunized with OVA alone, at day 22 of the immunization schedule (FIG. 3).

Example 3

Effect of the Co-Administration of GHRP-6 on the Humoral Immune Response Against C2 Antigen The C2 antigen, a Dengue virus capsid protein, was obtained as a recombinant protein in *Escherichia coli*, with a molecular weight of 15 kDa. To evaluate the humoral and cellular immune response in mice vaccinated with C2, in presence or absence of GHRP-6, 24 female BALB/c mice, 6-weeks old, were selected. They were distributed into 3 groups. Each animal was given an immunogen, according to the experimental group:

Group 1:10 µg C2
Group 2: 10 µg C2 co-administrated with 10 µg GHRP-6
Grupo 3: PBS In all groups, the immunogens further comprised aluminum hydroxide, also known as alum. Immunizations were performed by s.c route, on days 0, 15 and 30 of the immunization schedule. Blood samples were taken at days 0 (pre-immune), 7, 16, 21, 28 and 35, to assess total IgG titers.

Figure 4:
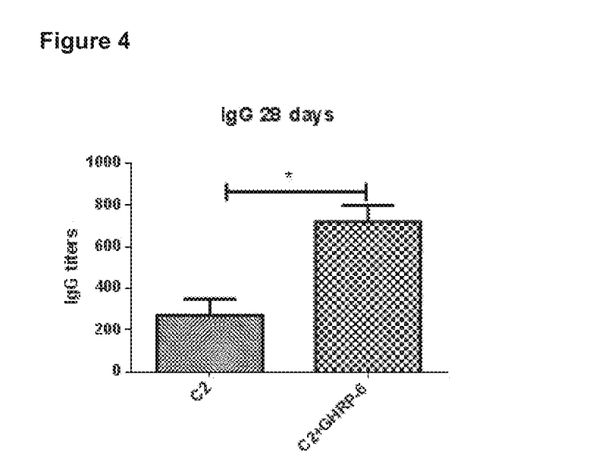
FIG. 4. IgG titers (detected on day 28 of the immunization schedule) in groups immunized with C2 and aluminum; or with C2, GHRP-6 and aluminum, by s.c route. The median and the standard deviation within each group are represented. * indicates $p<0.05$.

FIG. 4 shows that, on day 28 of the immunization schedule, Group 2, treated with C2 and GHRP-6, showed a significant increase in anti-C2 IgG titer, compared to Group 1, treated with C2 and the adjuvant aluminum hydroxide, without GHRP-6.

Example 4

Effect of the Co-Administration of GHRP-6 on the Humoral Immune Response Against the Peptide P0 of *R. sanguineus*

The peptide P0 is a fragment corresponding to the region of less sequence identity between the ribosomal protein P0 of the tick *R. sanguineus* and its mammalian host. To evaluate the humoral immune response stimulated by the co-administration of GHRP-6 and P0, 24 female, 6-week old BALB/c mice were selected and divided into three groups of 8 mice. Each animal received 150 μL of immunogen, by i.p route, on days 1, 15 and 29 of the immunization schedule. In the first immunization FCA was employed, and FIA was used in the other two administrations.

Group 1. Control (PBS)
Group 2. 100 μg of P0.
Group 3. 100 μg of P0 co-administrated with 200 μg of GHRP-6.

Figure 5:
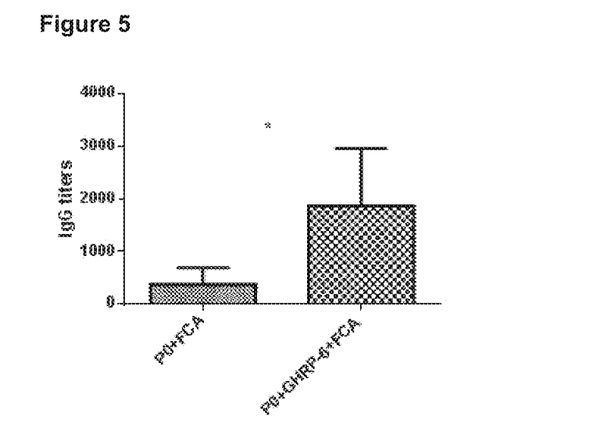
FIG. 5. IgG titers in mice immunized with P0 and Freund's adjuvant; or with P0, GHRP-6 and Freund's adjuvant by i.p route, on day 36 of the immunization schedule. The median and the standard deviation within each group are represented. * indicates $p<0.05$.

Blood samples were taken on days 0 (pre-immune serum), 8, 16, 21, 28, 36, 43, 50 and 58, to determine the levels of total IgG. In the animals immunized with P0, in the presence of GHRP-6, there was a significant increase in the IgG titers, if compared to those that did not receive GHRP-6, as seen in FIG. 5, which shows the anti-P0 antibody levels at 36 days of the schedule.

Example 5

Effect of the Co-Administration of GHRP-6 or the Peptide A233 on the Humoral Immune Response Against the P0-my32 Protein in Tilapia (*Oreochromis* sp.)

The chimeric protein P0-my32 was generated by cloning the complementary deoxyribonucleic acid (cDNA) encoding a 35 amino acid peptide of the *L. salmonis* P0 ribosomal protein fused to the N-terminal end of the cDNA encoding the my32 protein of the same ectoparasite (Carpio et al., 2013; *Exp. Parasitol* 135: 188-199), in a vector designed for the induced expression of genes of interest in the host bacterium *E. coli*. This protein was produced in the bacterium and purified, as a fusion protein with a tail of histidine, by metal chelate affinity chromatography.

For the accomplishment of the immunization experiment, 6 study groups of male juveniles of *Oreochromis niloticus*, were formed, with 15 animals each. In all groups, the immunogen was administered by i.p. route, adjuvanted with Montaide ISA 50.

The experimental groups received the following immunogens:

Group 1: PBS
Group 2: P0-my32 (1 μg/g of fish weight)
Group 3: P0-my32 (1 μg/g of fish weight) co-administrated with 20 μg GHRP-6
Group 4: P0-my32 (1 μg/g of fish weight) co-administrated with 20 μg A233
Group 5: P0-my32 (1 μg/g of fish weight). The fish in this group were fed with feed formulated with 100 μg of GHRP-6 per kg of feed, twice daily, for one week before and one week after the administration of my32 in injections.

During the course of the experiment, the fish in groups 1 to 4 were fed twice daily with a balanced unmedicated commercial formula, at the rate of 1% of their body weight. Immunizations were performed on days 0 and 14 of the schedule. Blood samples were taken at days 0, 21, 28 and 35 from the start of the experiment.

Figure 6:
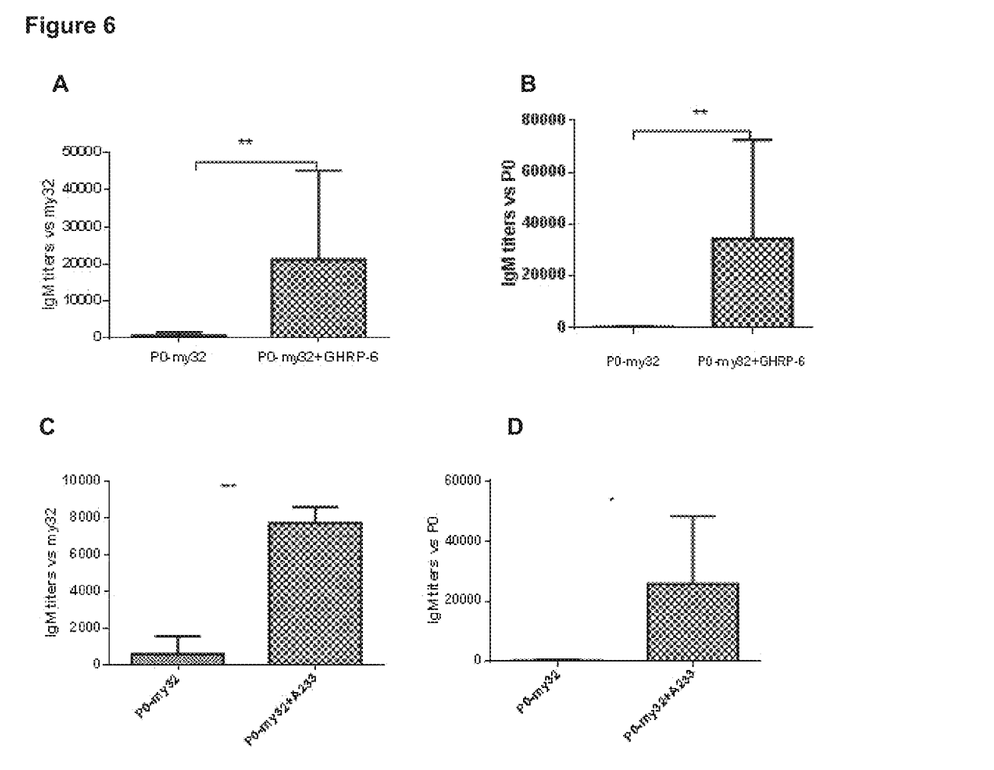
FIG. 6. Immunoglobulin M (IgM) titers in tilapias immunized with P0-my32 or with P0-my32 combined with GHRP-6 or with the peptide A233, detected on day 28 of the experiment, the immunogens were administered by i.p. route. A. and C. Titers of IgM against my-32. B and D. Titers of IgM against P0. In A and B the titers in animals treated with or without GHRP-6 are shown, while in C and D the titers in animals treated with or without A233 are presented. The median and the standard deviation within each group are represented. * indicates $p<0.01$;  indicates $p<0.0014$; * indicates $p<0,001$.

In tilapias injected with P0-my32 in the presence of GHRP-6 there was an increase in anti-my32 IgM antibody titers, compared to the group injected with P0-my32. This increase was statistically significant, as shown in FIG. 6A, which shows the levels of antibodies in sera extracted on day 28. The same effect was observed for anti-P0 IgM titer (FIG. 6B). Co-administration of A233 with the chimeric antigen also allowed an increase in IgM titers against the two components, as compared to the control group (FIGS. 6C and 6D). The group injected with P0-my32 and simultaneously fed with feed containing GHRP-6 also showed an increase in the titers, if compared to the group injected with the chimeric protein, which was fed with an unmodified feed (Table 2).

TABLE 2

Effect on anti-my32 and anti-P0 IgM titers of the co-administration of GHRP-6 in feed

| IgM titers | Group 2 | Group 5 |
|---|---|---|
| Anti-my32 | 601.0 ± 484.8 | 5760 ± 1866* |
| Anti-P0 | 200.0 ± 150.0 | 6600 ± 2229* |

*indicates significant differences between the groups p < 0.05.

Figure 7:
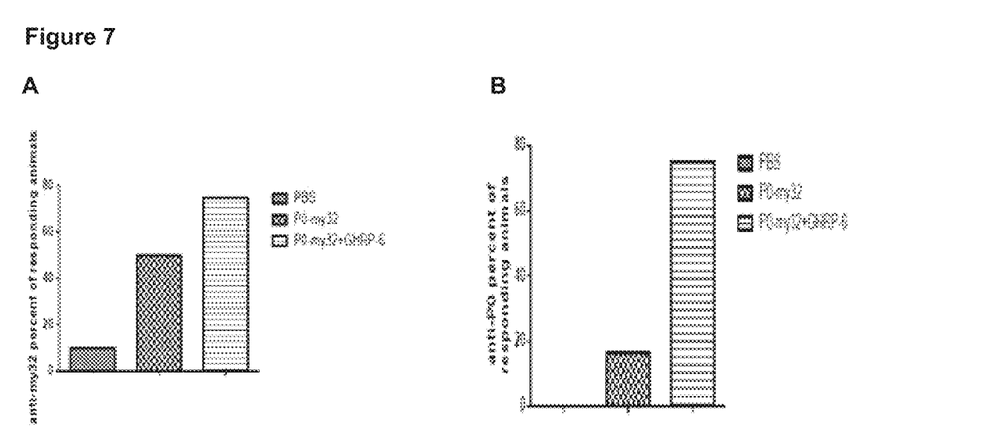
FIG. 7. Percent of tilapias with IgM titers greater than 1:1000, after the immunization with a P0-my32 formulation including Montanide ISA 50 or P0-my32 including GHRP-6 and Montanide ISA 50, at day 28 of the experiment. A. Percentage of anti-my32 responder animals. B. Percentage of anti-P0 responder animals.

In addition, in the group injected by i.p route with immunogen containing GHRP-6 (Group 3), the number of responder animals, with IgM titers greater than 1:1000, was higher for both components of the chimeric protein, compared to the group treated with P0-my32 that did not receive the peptide GHRP-6 (Group 2). It can be seen in FIGS. 7A and 7B.

Example 6

Effect of the Co-Administration of GHRP-6 or A233 and the P0-TT Protein on the Humoral Immune Response in Clarias (*Clarias gariepinus*)

The chimeric protein P0-TT is based on: a) the peptide named pP0, composed by 35 amino acids, corresponding to the region less conserved between the *L. salmonis* P0 ribosomal protein and the same protein in one of its hosts, *Salmo salar* and b) two T cell epitopes, coming from the measles virus and tetanus toxoid, respectively. For the experiment, 4 study groups of *C. gariepinus* were formed, with 12 animals in each one. These animals were immunized by i.p. route with 1 μg of the P0-TT protein per gram of animal weight (Group 2) or with the same dose of the chimeric protein P0-TT (1 μg/g of animal weight) co-administered with 20 μg of either GHRP-6 or A233 per animal (Groups 3 and 4, respectively), in a total volume of 120 μL. The control group (Group 1) received the same volume of PBS. The immunogens corresponding to all groups were emulsified with Montanide ISA 50 oily adjuvant. The immunization was performed under the same conditions, on days 0 and 14 of the administration schedule. Blood samples were taken at days 0, 21, 28 and 35 counted from the start of the experiment.

Figure 8:
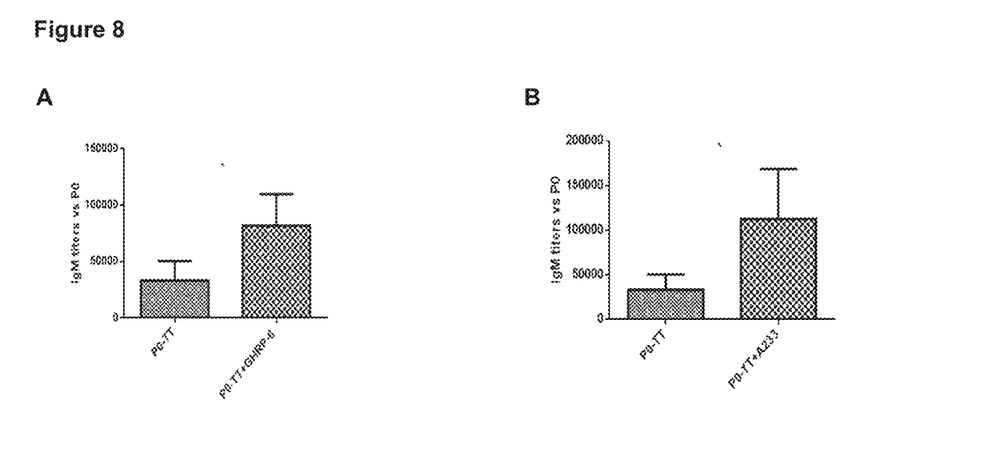
FIG. 8. Response of IgM antibodies in claria immunized with P0-TT or with P0-TT in presence of GHRP-6 or peptide A233, on day 28 of the experiment, where the fish were immunized by i.p. route. A. Anti-P0 titers in the groups of the evaluation experiment with GHRP-6 as an adjuvant. B. Anti-P0 titers in the groups of the evaluation experiment with A233 as an adjuvant. All immunogens were combined with Montanide ISA 50.

In clarias immunized with P0-TT and GHRP-6 there was an increase in anti-P0 IgM antibody titers, when it as compared to the group injected with P0-TT without the GHRP-6 peptide, which had statistical significance at day 28 (FIG. 8A). The same effect was observed for the titers obtained after administration of P0-TT and A233 (FIG. 8B).

Example 7

Demonstration of the Adjuvant Effect of GHRP-6 on the Humoral Immune Response of Common Carp (*Cyprinus carpio*) Against the Bacterium *Aeromonas hydrophila*

The experiment was carried out with carps (*C. carpio*) of 40±10 g. These animals were kept in 600 L aquaria, at a temperature of 28±2° C. Three experimental groups, of 10 carps each, were established and injected by i.p. route with the following immunogens:

Group 1: PBS+Montanide ISA 50.
Group 2: Inactivated *A. hydrophila* cells ($1 \times 10^8$ Colony Forming Units, abbreviated CFU)+Montanide ISA 50.
Group 3: Inactivated *A. hydrophila* cells ($1 \times 10^8$ CFU)+20 μg GHRP-6/fish+Montanide ISA 50.

Figure 9:
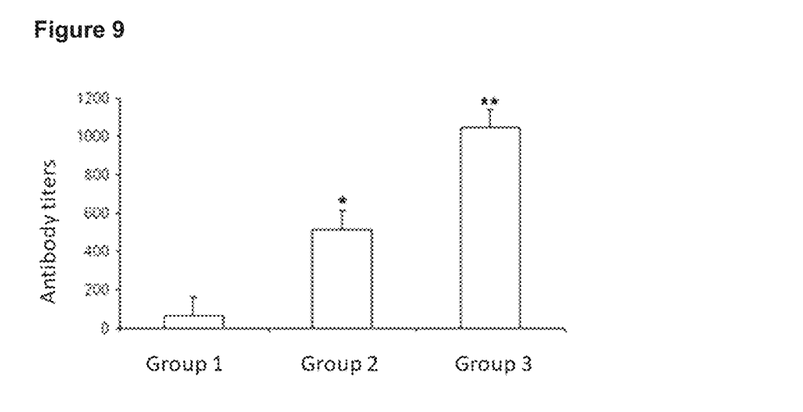
FIG. 9. Titers of agglutinating antibodies against *Aeromonas hydrophila* in common carp. The Y-axis values represent median±standard error. * indicates p<0.05; ** indicates p<0.01. Group 1: Injected with PBS, Group 2: Injected with formalin inactivated *A. hydrophila* cells, Group 3: Injected with formalin inactivated *A. hydrophila* cells and GHRP-6 (20 µg per fish). All immunogens were combined with Montanide ISA 50.

Fish were injected on days 0 and 14, and blood samples were collected from the caudal vein on days 0 and 21. The results showed that the titers of agglutinating antibodies against *A. hydrophila* were significantly higher in the group immunized with the bacterium and GHRP-6, compared to the group immunized with the bacterium without the GHRP-6 peptide (FIG. 9). These results corroborate the effect of GHRP-6 as a molecular adjuvant in fish. The preparation of *A. hydrophila* cells and the measurement of antibody titers were performed according to previous reports (Yin et al. ((1996) *Fish & Shellfish Immunol.* 6, 57-69).

Example 8

Controlled Challenge Experiment in Fish Immunized with the Inactivated *Aeromonas hydrophila* Bacterium and the Inactivated Bacterium Co-Administered with the GHRP-6 peptide The experiment was carried out with common carp (*C. carpio*) of 30±5 g. These animals were kept in 250 L aquaria, at a temperature of 30±2° C. Three experimental groups, of 20 carps each, were established and the animals were injected by i.p. route with:

Group 1: PBS+Montanide ISA 50
Group 2: Inactivated *A. hydrophila* cells ($1 \times 10^8$ CFU)+ Montanide ISA 50
Group 3: Inactivated *A. hydrophila* cells ($1 \times 10^8$ CFU)+20 μg GHRP-6/fish+Montanide ISA 50.

Fish were injected on day 0 and 14. The challenge was performed on day 21, by i.p injection of the lethal dose 50 (LD50) of the bacterium, and the mortality in each group was recorded for 7 days. The relative survival rate (RSR) was calculated as:

RSR(%)=(% mortality of controls–% mortality of treated animals)/(% mortality of controls)×100.

As a result, 65% of RSR was obtained in Group 2, and 95% of RSR in Group 3, demonstrating that administration of GHRP-6 increases the survival rate in fish vaccinated and challenged with the pathogen.

Example 9

Demonstration of the Adjuvant Effect of GHRP-6 on the Humoral Immune Response Of Chickens Against Bovine Serum Albumin Fifteen neonatal broiler chickens, hybrid EB34 Cronish× White Plymoth Rock-type, were used, and they were divided into three experimental groups of 5 animals each. Animals were immunized by i.p route, on days 12 and 18 of the immunization schedule, with 5 μg of BSA per animal (Group 2), or with 5 μg of BSA and 20 μg of GHRP-6 per animal (Group 3). The control group (Group 1) was immunized with PBS. The levels of IgY antibodies in serum were determined, on day 25 of the experiment. There were statistically significant differences between the antibody titers in the animals of the BSA-immunized group and in the one that received BSA and GHRP-6 (Table 3).

TABLE 3

Response of antigen-specific IgY antibodies in the serum of chickens immunized with BSA.

| Group | Immunogen | IgY |
| --- | --- | --- |
| 1 | PBS | 0.10 ± 0.08 |
| 2 | BSA | 0.47 ± 0.06 |
| 3 | BSA + GHRP-6 | 0.65 ± 0.07 |

The data show the mean and the standard deviation of the maximum values of absorbance determined by indirect ELISA.

INCORPORATION OF SEQUENCE LISTING

Incorporated herein by reference in its entirety is the Sequence Listing for the application. The Sequence Listing is disclosed on a computer-readable ASCII text file titled, "SequenceListing_976-103PCTUS.txt", created on May 6, 2020. The file is 1018 kb in size.

The invention claimed is:

1. A vaccine composition comprising a growth hormone secretagogue peptide consisting of SEQ ID No. 1 or SEQ ID No. 2, at least one vaccine antigen, and pharmaceutically acceptable vehicles or diluents, wherein the growth hormone secretagogue peptide is in an amount sufficient to stimulate host immune response to the vaccine antigen.

2. The composition of claim 1 wherein the at least one vaccine antigen is selected from the group consisting of peptides, proteins, viruses and attenuated bacteria.

3. The composition of claim 2, wherein said composition is administered in mammals, birds or fish, orally or by injection.

4. The composition of claim 3 wherein the peptide of sequence SEQ ID No. 1 or SEQ ID No. 2 is in a concentration of 50-600 µg/Kg of formulated feed when the composition is orally administered to fish.

5. A method for increasing an immune response against a vaccine antigen, wherein an effective amount of a growth hormone secretagogue peptide consisting of SEQ ID No. 1 or SEQ ID No. 2 is administered as a molecular adjuvant of said antigen.

6. The method of claim 5 wherein the vaccine antigen is used for the prevention of diseases caused by infectious agents.

7. The method of claim 5 wherein the peptide of sequence SEQ ID No. 1 or SEQ ID No. 2 is used at 50-600 µg/Kg of formulated feed when the vaccine antigen and the molecular adjuvant peptide are administered by oral route.

8. The method of claim 5 wherein the peptide of sequence SEQ ID No. 1 or SEQ ID No. 2 is employed at 0.1-40 µg/g of animal body weight, when the vaccine antigen and the molecular adjuvant peptide are administered by injections.

* * * * *

SEQUENCE LISTING

```
<160> NUMBER OF SEQ ID NOS: 2

<210> SEQ ID NO 1
<211> LENGTH: 6
<212> TYPE: PRT
<213> ORGANISM: Artificial Sequence
<220> FEATURE:
<223> OTHER INFORMATION: Description of the Artificial Sequence:GHRP-6,
      Trp(2) and Phe(5) are D amino acids
<220> FEATURE:
<221> NAME/KEY: MOD_RES
<222> LOCATION: (6)
<223> OTHER INFORMATION: AMIDATION

<400> SEQUENCE: 1

His Trp Ala Trp Phe Lys
1               5

<210> SEQ ID NO 2
```

```
<211> LENGTH: 10
<212> TYPE: PRT
<213> ORGANISM: Artificial Sequence
<220> FEATURE:
<223> OTHER INFORMATION: Description of the Artificial Sequence:peptide
      A233, comprise a lactam bond between Lys and Asp

<400> SEQUENCE: 2

Gly Lys Phe Asp Leu Ser Pro Glu His Gln
1               5                   10
```